US011181753B2

(12) United States Patent
Obata et al.

(10) Patent No.: US 11,181,753 B2
(45) Date of Patent: Nov. 23, 2021

(54) CONTACT LENS PACKAGE AND METHOD FOR PRODUCING THE SAME

(71) Applicant: MENICON CO., LTD., Nagoya (JP)

(72) Inventors: Azusa Obata, Nagoya (JP); Susumu Ogawa, Toki (JP); Masaki Baba, Kasugai (JP)

(73) Assignee: MENICON CO., LTD., Nagoya (JP)

( * ) Notice: Subject to any disclaimer, the term of this patent is extended or adjusted under 35 U.S.C. 154(b) by 258 days.

(21) Appl. No.: 15/760,146

(22) PCT Filed: Sep. 30, 2015

(86) PCT No.: PCT/JP2015/077746
§ 371 (c)(1),
(2) Date: Mar. 14, 2018

(87) PCT Pub. No.: WO2017/056235
PCT Pub. Date: Apr. 6, 2017

(65) Prior Publication Data
US 2019/0049751 A1 Feb. 14, 2019

(51) Int. Cl.

| | |
|---|---|
| ***G02C 7/04*** | (2006.01) |
| ***A61L 12/00*** | (2006.01) |
| ***G02B 1/04*** | (2006.01) |
| ***B29D 11/00*** | (2006.01) |
| ***C11D 1/72*** | (2006.01) |
| ***G02C 13/00*** | (2006.01) |
| *C08F 283/12* | (2006.01) |

(52) U.S. Cl.
CPC .............. *G02C 7/049* (2013.01); *A61L 12/00* (2013.01); *B29D 11/00038* (2013.01); *C11D 1/72* (2013.01); *G02B 1/043* (2013.01); *G02C 7/04* (2013.01); *G02C 13/00* (2013.01); *C08F 283/12* (2013.01)

(58) Field of Classification Search
CPC . A61L 12/00; B29D 11/00038; C08F 283/12; C11D 1/72; G02B 1/043; G02C 13/00; G02C 7/04; G02C 7/049
See application file for complete search history.

(56) References Cited

U.S. PATENT DOCUMENTS

2002/0071789 A1 6/2002 Molock et al.
2004/0186248 A1* 9/2004 Vanderlaan ........... C08F 230/08 525/474
2005/0171232 A1 8/2005 Ford et al.
2010/0226963 A1 9/2010 Cooper et al.
2012/0148519 A1* 6/2012 Satake .................. G02B 1/043 424/78.04
2013/0274332 A1 10/2013 Furumiya et al.

FOREIGN PATENT DOCUMENTS

| | | | |
|---|---|---|---|
| CN | 103269686 | A | 8/2013 |
| JP | 2004-523777 | A | 8/2004 |
| JP | 2005-053905 | A | 3/2005 |
| JP | 2007-512554 | A | 5/2007 |
| JP | 2014-015453 | A | 1/2014 |
| JP | 2014-210813 | A | 11/2014 |
| JP | 2015-026039 | A | 2/2015 |
| JP | 2015-091880 | A | 5/2015 |

OTHER PUBLICATIONS

Dec. 22, 2015 International Search Report issued in International Patent Application No. PCT/JP2015/077746.
Apr. 3, 2018 International Preliminary Report on Patentability issued in Patent Application No. PCT/JP2015/077746.

* cited by examiner

*Primary Examiner* — Yan Lan
(74) *Attorney, Agent, or Firm* — Oliff PLC

(57) ABSTRACT

A contact lens package includes a silicone hydrogel contact lens, a packaging container composed of a polypropylene, and a packaging solution containing a nonionic surfactant, the nonionic surfactant including a linear alkyl moiety having 12 or more carbon atoms and an oxyethylene moiety, the average addition mole number of oxyethylene being 30 or more per mole of the nonionic surfactant.

9 Claims, No Drawings

CONTACT LENS PACKAGE AND METHOD FOR PRODUCING THE SAME

TECHNICAL FIELD

The present invention relates to a contact lens package and a method for producing the contact lens package.

BACKGROUND ART

Hitherto, a contact lens package including a packaging solution, used for hydrophobic contact lenses, containing polysorbate or poloxamer serving as a surfactant has been reported (for example, see PTL 1). The packaging solution can substantially prevent the sticking of a lens to a surface of a packaging material. A contact lens package in which a soft lens is stored in a packaging solution containing methyl cellulose serving as a surfactant has been reported (for example, see PTL 2). The packaging solution can inhibit the sticking of the soft lens to a hydrophobic packaging material.

CITATION LIST

Patent Literature

PTL 1: Japanese Unexamined Patent Application Publication (Translation of PCT Application) No. 2004-523777

PTL 2: Japanese Unexamined Patent Application Publication (Translation of PCT Application) No. 2007-512554

SUMMARY OF THE INVENTION

Technical Problem

However, the packaging solution disclosed in PTL 1 cannot inhibit the sticking of a flexible lens to a packaging container. In PTL 2, because methyl cellulose used as a surfactant has low solubility in water, for example, heating is required for dissolution. Furthermore, there are problems of contamination with impurities and low productivity due to poor filterability.

In recent years, more flexible silicone hydrogel contact lenses with low elastic modulus (Young's modulus) have been investigated in order to improve wearing comfort. Such a material has an increased area of contact with a packaging container because of its flexibility, and easily sticks to a highly hydrophobic packaging container. This increases the possibility of occurrence of the deformation and breakage of contact lenses.

The present invention has been accomplished in light of the foregoing problems and mainly aims to provide a contact lens package having the effect of inhibiting adhesion between a silicone hydrogel contact lens and a packaging container composed of polypropylene and to a method for producing the contact lens package.

The inventors have conducted intensive studies in order to achieve the foregoing objects and have found that the use of a packaging solution containing a predetermined amount of a predetermined nonionic surfactant is highly effective in inhibiting the adhesion. This finding has led to the completion of the present invention.

A contact lens package according to the present invention includes:

a silicone hydrogel contact lens;

a packaging container composed of a polypropylene; and a packaging solution containing a nonionic surfactant, the nonionic surfactant including a linear alkyl moiety having 12 or more carbon atoms and an oxyethylene moiety, the average addition mole number of oxyethylene being 30 or more per mole of the nonionic surfactant.

A method for producing a contact lens package according to the present invention includes:

sealing a silicone hydrogel contact lens and a packaging solution in a packaging container composed of a polypropylene, the packaging solution containing a nonionic surfactant, the nonionic surfactant including a linear alkyl moiety having 12 or more carbon atoms and an oxyethylene moiety, the average addition mole number of oxyethylene being 30 or more per mole of the nonionic surfactant.

Advantageous Effects of Invention

In the contact lens package of the present invention and the method for producing the contact lens package, it is possible to further inhibit sticking (adhesion) of the silicone hydrogel contact lens to the packaging container composed of polypropylene. The reason for this is presumably as follows: For example, the nonionic surfactant has the linear alkyl moiety having 12 or more carbon atoms, and the average addition mole number of oxyethylene is 30 or more; thus, the nonionic surfactant has a good affinity for a hydrophobic portion of the silicone hydrogel. In general, silicone hydrogels have high hydrophobicity. Thus, the silicone hydrogel seems to interact strongly with a hydrophobic portion of the nonionic surfactant in water. Thereby, a hydrophilic unit of the surfactant attracted to surfaces of the lens seems to be directed toward the surfaces (in the solution) to impart hydrophilicity to the surfaces of the lens. However, when the nonionic surfactant has excessively strong hydrophilicity, the surfactant itself is not attracted to the lens; thus, a difficulty lies in imparting hydrophilicity to the surfaces of the lens. When the nonionic surfactant has excessively strong hydrophobicity, the surfactant itself can strongly adhere to the lens; however, a difficulty lies in imparting sufficient hydrophilicity to the lens. Accordingly, a balance between the hydrophobicity and the hydrophilicity is significantly important. In the present invention, it is speculated that the nonionic surfactant has a good balance between the hydrophobicity and the hydrophilicity and effectively provides the effect of inhibiting the adhesion.

DESCRIPTION OF EMBODIMENTS

The contact lens package of the present invention includes a silicone hydrogel contact lens, a packaging container composed of a polypropylene, and a packaging solution containing a nonionic surfactant. The nonionic surfactant in the packaging solution has a linear alkyl moiety having 12 or more carbon atoms and an oxyethylene moiety. The average addition mole number of oxyethylene is 30 or more per mole of the nonionic surfactant. The term "linear alkyl moiety" indicates that the carbon atoms have not a ring or branched structure but a structure in which the carbon atoms are connected together to form a single chain.

As the silicone hydrogel contact lens, a known lens may be used. Regarding the silicone hydrogel contact lens, for example, polymers containing a silicone monomer copolymerized with a hydrophilic monomer are used. Examples of a material used for the production of such a silicone hydrogel include acquafilcon A, asmofilcon A, balafolcon A, enfilcon A, galyfilcon A, lenefilcon A, lotorafilcon A, lotorafilcon B, senofilcon A, comfilcon A, stenfilcon A, and narafilcon A. Examples of the silicone monomer contained in the silicone hydrogel include 3-(meth)acryloyloxypropyltris(trimethylsiloxy)silane, mono(meth)acryloyloxypropyl terminated poly(dimethylsiloxane), 3-(meth)acryloyloxypropylbis(trimethylsiloxy)methylsilane, and (meth)acryloyloxypropylpentamethyldisiloxane. Of these, 3-methacryloyloxypropyltris(trimethylsiloxy)silane (TRIS) is more preferred because it has good compatibility with another monomer, can be distilled, and is easily obtained with high purity.

An example of a material used for the production of the silicone hydrogel is a silicone macromer. The silicone macromer may be, for example, a compound having a urethane structure, an ethylenically unsaturated structure, polydimethylsiloxane structure, and a polymerizable group. The polymerizable group may be, for example, one or more of an acryloyl group and a methacryloyl group. The silicone macromer may have, for example, a structure represented by chemical formula (1). In formula (1), c preferably represents 30 or more and 50 or less. An example of the silicone macromer is a compound represented by chemical formula (2). The silicone macromer may be a compound represented by chemical formula (3).

[Chem. 1]

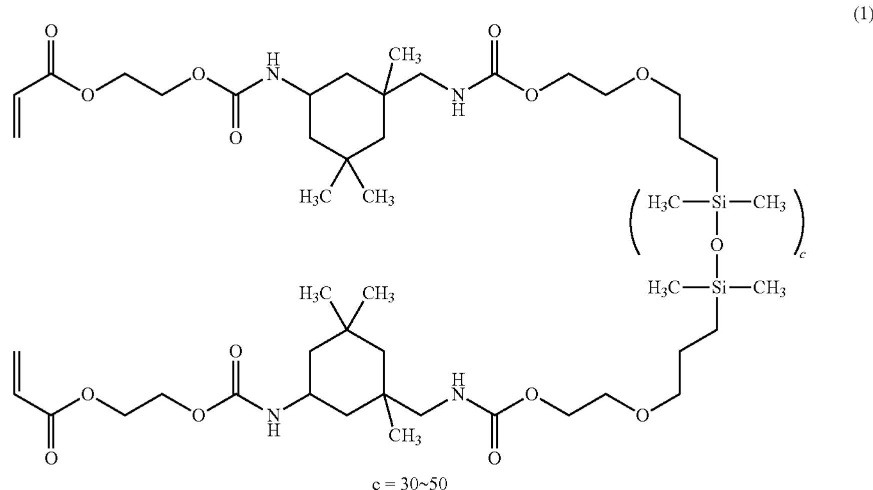

[Chem. 2]

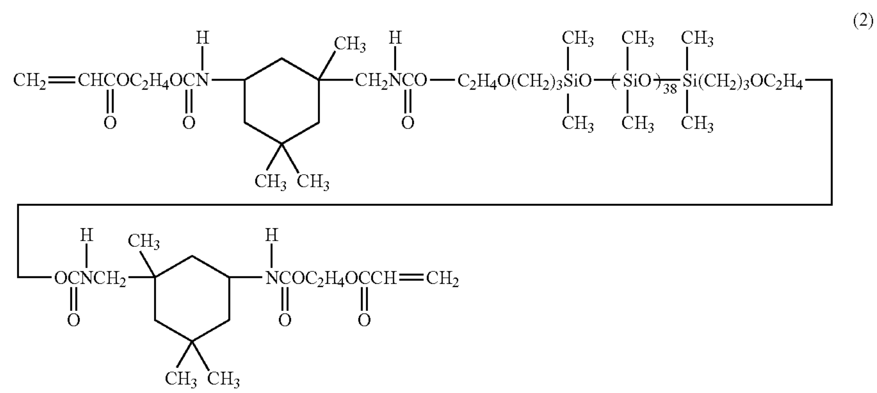

-continued

[Chem. 3]

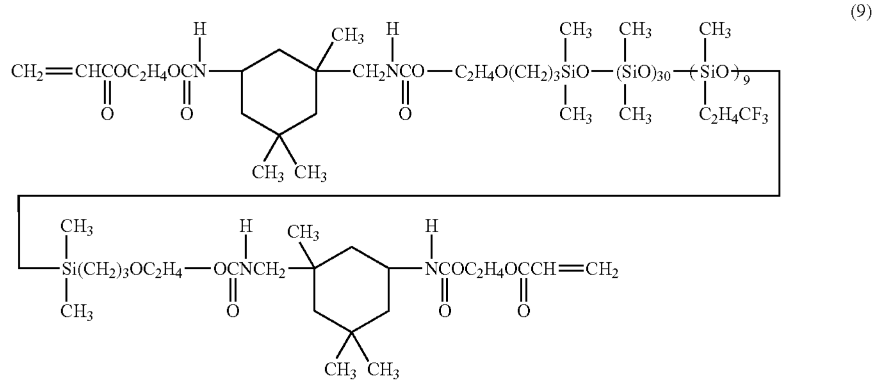

(9)

Examples of the hydrophilic monomer contained in the silicone hydrogel include unsaturated carboxylic acids such as methacrylic acid and acrylic acid, acrylic-substituted alcohols such as 2-hydroxyethyl methacrylate and 2-hydroxyethyl acrylate, vinyl lactams such as 1-methyl-3-methylene-2-pyrrolidone and N-vinylpyrrolidone, acrylamides such as methacrylamide and N,N-dimethylacrylamide, and (meth)acrylates having a polyethylene glycol moiety. Of these, for example, N-vinylpyrrolidone, N,N-dimethylacrylamide, and 1-methyl-3-methylene-2-pyrrolidone are preferred because these have good compatibility with another monomer and can impart high hydrophilicity to the hydrophobic silicone hydrogel in small amounts.

The silicone hydrogel contact lens preferably has a Young's modulus of 1.2 MPa or less. At a Young's modulus of 1.2 MPa or less, the lens is flexible and further inhibits hyperemia that can be caused by allowing the lens and an eye to rub against each other, which is preferred. The Young's modulus is more preferably 1.1 MPa or less from the viewpoint of further improving wearing comfort. When the silicone hydrogel contact lens has a Young's modulus of more than 1.2 MPa, particularly 1.4 MPa or more, the lens is relatively hard, and the area of contact with the packaging container is not easily increased; thus, the sticking of the contact lens to the packaging container does not easily occur. The contact lens package of the present invention is further effective for a further flexible silicone hydrogel contact lens having a Young's modulus of, for example, less than 1.4 MPa.

The silicone hydrogel contact lens may be subjected to surface modification treatment. The surface modification treatment can further enhance the water wettability of the silicone hydrogel contact lens. Examples of the surface modification treatment that can be employed include low-temperature plasma treatment, atmospheric-pressure plasma, and corona discharge known to those skilled in the art. The surface modification treatment may be performed at atmospheric or reduced pressure. For example, in the case of low-temperature plasma treatment or the like under reduced pressure, one or more selected from alkanes having 1 to 6 carbon atoms, fluorine-substituted alkanes, $O_2$, $N_2$, $CO_2$, argon, hydrogen, air, water vapor, and so forth may be used as a carrier gas.

Hitherto, polypropylene, polyethylene, nylon, olefin, copolymers, acrylic resins, rubber, urethane, polycarbonate, and fluorocarbon resins have been studied for the packaging container. The packaging container is preferably composed of polypropylene in view of low water vapor permeability, resistance to high-pressure steam sterilization, durability, low raw material cost, and transparency. The packaging container has a storage portion to store the silicone hydrogel contact lens. The packaging container preferably includes a lid sheet that fluid-tightly covers and seals the opening of the lens storage portion of the packaging container. The lid sheet is formed of, for example, a laminated sheet composed of a composite material in which aluminum foil and a synthetic resin that has been formed into a layer or foil are integrally stacked.

The packaging solution contains the nonionic surfactant including the linear alkyl moiety having 12 or more carbon atoms and the oxyethylene moiety, the average addition mole number of oxyethylene being 30 or more per mole of the nonionic surfactant. The presence of the nonionic surfactant in the packaging solution further inhibits the sticking of the silicone hydrogel contact lens to the packaging container. When the number of carbon atoms of the linear alkyl moiety in the nonionic surfactant is 12 or more, hydrophobicity is sufficiently provided, which is preferred also from the viewpoint of availability. The number of carbons is more preferably 15 or more, even more preferably 17 or more. The number of carbons is preferably 20 or less in view of solubility in the solution. Because the silicone hydrogel has a hydrophobic portion, the nonionic surfactant preferably has a linear alkyl moiety that can provide a certain extent of hydrophobicity in order to provide the effect of inhibiting the adhesion between the contact lens and the packaging container. To provide hydrophobicity to a necessary and sufficient extent, the alkyl chain preferably has 12 or more and 20 or less carbon atoms. The average addition mole number of oxyethylene of the nonionic surfactant is preferably 30 or more, more preferably 40 or more in view of solubility in the solution and the impartation of hydrophilicity. The average addition mole number of oxyethylene is preferably 100 or less in view of availability. An example of the nonionic surfactant is polyoxyethylene hydrogenated castor oil. Examples of the polyoxyethylene hydrogenated castor oil include polyoxyethylene hydrogenated castor oil 40 (average addition mole number of oxyethylene=40), polyoxyethylene hydrogenated castor oil 60 (average addition mole number of oxyethylene=60), and polyoxyethylene hydrogenated castor oil 100 (average addition mole number of oxyethylene=100).

The packaging solution preferably has a nonionic surfactant content of 0.001% or more by mass and 0.1% or less by mass. At a nonionic surfactant content of 0.001% or more by mass, the effect of inhibiting the adhesion between the contact lens and the packaging container can be more significantly provided. To provide the intended effect, the nonionic surfactant content is more preferably 0.005% or more by mass. At a nonionic surfactant content of 0.1% or less by mass, because an excessive content of the nonionic surfactant is not used, for example, the occurrence of foaming can be further inhibited, facilitating the production. Furthermore, excessive swelling of the contact lens can be inhibited; thus, the contact lens is easily removed from the packaging container, which is preferred. The nonionic surfactant content is more preferably 0.08% or less by mass.

The packaging solution may contain an additive in addition to the nonionic surfactant as long as the effect of the present invention is not impaired. Examples of the additive include chelating agents, isotonizing agents, pH adjusters, buffers, surfactants, thickeners, bacteriostatic agents (preservatives), and wetting agent. These additives may be added alone to the packaging solution or in combination of two or more thereof to the packaging solution.

Examples of the chelating agent include ethylenediaminetetraacetic acid (EDTA) and its hydrate, disodium ethylenediaminetetraacetate (EDTA·2Na) and its hydrate, trisodium ethylenediaminetetraacetate (EDTA·3Na) and its hydrate, tetrasodium ethylenediaminetetraacetate (EDTA·4Na) and its hydrate, phytic acid, and citric acid. The amount of the chelating agent incorporated in the packaging solution is preferably 0% or more by mass and 1.0% or less by mass. When the amount of the chelating agent incorporated is 1.0% or less by mass, the eyes of a user are less likely to be affected during the wearing of the contact lenses. The amount incorporated is preferably 0.001% or more by mass. When the amount incorporated is 0.001% or more by mass, the chelating agent can be more effective.

Examples of the isotonizing agent include for example, glycerol, propylene glycol, sodium chloride, potassium chloride, sorbitol, and mannitol. The amount of the isotonizing agent incorporated in the packaging solution is preferably 0% or more by mass and 2.0% or less by mass. When the amount incorporated is 2.0% or less by mass, eye safety is high, and effects such as eye irritation and a feeling of a foreign body are less likely to be caused during the wearing of the contact lens of a user. The amount incorporated is preferably 0.01% or more by mass. When the amount incorporated is 0.01% or more by mass, the isotonizing agent can be more effective.

Examples of the pH adjuster include hydrochloric acid, citric acid, acetic acid, sodium hydroxide, potassium hydroxide, sodium carbonate, and sodium bicarbonate. The amount of the pH adjuster incorporated in the packaging solution is preferably 0% or more by mass and 1.0% or less by mass. When the amount incorporated is 1.0% or less by mass, the eyes of a user are less likely to be caused during the wearing of contact lenses. The amount incorporated is preferably 0.01% or more by mass. When the amount incorporated is 0.01% or more by mass, the pH adjuster can be more effective.

Examples of the buffer include phosphoric acid, phosphate buffers, boric acid, borax, borate buffers, carbonate buffers, acetic acid, citric acid, ε-aminocaproic acid, 2-amino-2-methyl-1,3-propane (AMP) buffers, tris(hydroxymethyl)aminomethane (Tris) buffers, and bis(2-hydroxyethyl)iminotris(hydorxymethyl)methane (Bis-Tris). The amount of the buffer in the packaging solution is preferably 0% or more by mass and 2.0% or less by mass. When the amount incorporated is 2.0% or less by weight, eye safety is high, and effects such as eye irritation and a feeling of a foreign body are less likely to be caused during the wearing of the contact lens of a user. The amount incorporated is preferably 0.01% or more by mass. When the amount incorporated is 0.01% or more by mass, the buffer can be more effective.

Examples of the surfactant include polyglycerol fatty acid esters, polyoxyethylene alkyl ether, polyoxyethylene-polyoxypropylene block copolymers, polyoxyethylene-polyoxypropylene-ethylenediamine, polyoxyethylene alkyl phenyl ethers, polyoxyethylene alkyl phenyl ether-formaldehyde condensation products, polyoxyethylene alkyl phenyl ethers, polyoxyethylene glycerol fatty acid esters, polyoxyethylene sorbitol fatty acid esters, polyoxyethylene hydrogenated castor oil, polyoxyethylene sterols, polyoxyethylene hydrogenated sterols, polyoxyethylene fatty acid esters, polyoxyethylene-polyoxypropylene alkyl ethers, polyoxyethylene lanoline alcohols, polyoxyethylene alkylamines, polyoxyethylene alkylamides, polyoxyethylene alkyl ether phosphate, and polysorbates. The amount of the surfactant incorporated in the packaging solution is preferably 0% or more by mass and 1.0% or less by mass. When the amount incorporated is 1.0% or less by mass, eye safety is high, and effects such as eye irritation and a feeling of a foreign body are less likely to be caused during the wearing of the contact lens of a user. The amount incorporated is preferably 0.001% or more by mass. When the amount incorporated is 0.001% or more by mass, the surfactant can be more effective.

Examples of the thickener include poly(vinyl alcohol), poly(vinyl pyrrolidone), poly(ethylene glycol), poly(propylene glycol), polyacrylamide, cellulose derivatives such as hydroxymethyl cellulose and hydroxypropyl cellulose, starch derivatives, and synthetic organic polymer compounds. The amount of the thickener incorporated in the packaging solution is preferably 0% or more by mass and 1.0% or less by mass. When the amount incorporated is 1.0% or less by mass, eye safety is high, and effects such as eye irritation and a feeling of a foreign body are less likely to be caused during the wearing of the contact lens of a user. The amount incorporated is preferably 0.01% or more by mass. When the amount incorporated is 0.01% or more by mass, the thickener can be more effective.

Examples of the bacteriostatic agent (preservative) include sorbic acid, potassium sorbate, benzalkonium chloride, benzethonium chloride, methyl parahydroxybenzoate, propyl parahydroxybenzoate, and chlorobutanol. The amount of the bacteriostatic agent incorporated in the packaging solution is preferably 0% or more by mass and 1.0% or less by mass. When the amount incorporated is 1.0% or less by mass, eye safety is high, and effects such as eye irritation and a feeling of a foreign body are less likely to be caused during the wearing of the contact lens of a user. The amount incorporated is preferably 0.01% or more by mass. When the amount incorporated is 0.01% or more by mass, the bacteriostatic agent (preservative) can be more effective.

Examples of the wetting agent include glycerol, poly(ethylene glycol), poly(propylene glycol), poly(vinyl alcohol), poly(vinyl pyrrolidone), cationic cellulose polymers, hydroxypropyl cellulose, hydroxyethyl cellulose, and methyl cellulose. The amount of the wetting agent incorporated in the packaging solution is preferably 0% or more by mass and 1.0% or less by mass. When the amount incorporated is 1.0% or less by mass, eye safety is high, and effects such as eye irritation and a feeling of a foreign body are less likely to be caused during the wearing of the contact lens of a user. The amount incorporated is preferably 0.01% or more by mass. When the amount incorporated is 0.01% or more by mass, the wetting agent can be more effective.

The difference in relative density between the packaging solution and the silicone hydrogel contact lens is 0.1 or less at 20° C. In this range, for example, the deformation of the silicone hydrogel contact lens possibly caused by allowing the lens to float and to be exposed to air can be prevented or further inhibited. The difference in relative density refers to a value obtained by subtracting the relative density of the packaging solution from the relative density of the silicone hydrogel contact lens. The difference in relative density is preferably 0.08 or less, more preferably 0.06 or less.

The packaging solution preferably has a pH of 4.0 or more and 9.0 or less. When the pH of the packaging solution is in this range, for example, the degradation of the silicone hydrogel due to high-pressure sterilization treatment can be further inhibited to maintain the strength of the silicone hydrogel contact lens at a sufficient level. The pH is more preferably, for example, 5.0 or more and 8.0 or less.

The packaging solution preferably has an osmotic pressure of 200 mOsm or more and 500 mOsm or less, more preferably 250 mOsm or more and 400 mOsm or less. In this osmotic pressure range, for example, an effect such as eye irritation to a user is less likely to be caused, and a defect such as the deformation of the contact lens can be further prevented.

The packaging solution is preferably sealed in the packaging container in a volume of 0.01 ml or more and 5.0 ml or less, more preferably 0.1 ml or more and 2.5 ml or less.

A method for producing a contact lens package of the present invention includes the step of sealing a silicone hydrogel contact lens and a packaging solution in a packaging container composed of a polypropylene, the packaging solution containing a nonionic surfactant, the nonionic surfactant including a linear alkyl moiety having 12 or more carbon atoms and an oxyethylene moiety, the average addition mole number of oxyethylene being 30 or more per mole of the nonionic surfactant. In this production method, the foregoing embodiments of the silicone hydrogel contact lens, the packaging container, and the packaging solution may be appropriately used.

In the contact lens package according to the embodiment and the method for producing the contact lens package described above in detail, the sticking of the silicone hydrogel contact lens to the packaging container composed of polypropylene can be further inhibited. Because the sticking can be inhibited, the lens can be maintained at a fixed shape. Furthermore, phenomena such as the deformation and breakage of the contact lens, changes in optical properties, and the degradation of wearing comfort due to the sticking can be more effectively inhibited. The reason for this is presumably as follows: For example, the nonionic surfactant contained in the packaging solution has the linear alkyl moiety having 12 or more carbon atoms, and the average addition mole number of oxyethylene is 30 or more; thus the nonionic surfactant has a good affinity for a hydrophobic portion of the silicone hydrogel. In general, silicone hydrogels have high hydrophobicity. Thus, the silicone hydrogel seems to interact strongly with a hydrophobic portion of the nonionic surfactant in water. Thereby, a hydrophilic unit of the surfactant attracted to surfaces of the lens seems to be directed toward the surfaces (in the solution) to impart hydrophilicity to the surfaces of the lens. However, when the nonionic surfactant has excessively strong hydrophilicity, the surfactant itself is not attracted to the lens; thus, a difficulty lies in imparting hydrophilicity to the surfaces of the lens. When the nonionic surfactant has excessively strong hydrophobicity, the surfactant itself can strongly adhere to the lens; however, a difficulty lies in imparting sufficient hydrophilicity to the lens. The nonionic surfactant used in the present invention has a good balance between the hydrophobicity and the hydrophilicity and thus effectively provides the effect of markedly inhibiting the adhesion between the silicone hydrogel and the packaging container composed of polypropylene.

In general, in order to provide contact lenses appropriately matched with variations in the vision and the corneal shape of users, specifications such as lens dimensions, e.g., lens diameter (DIA), power (power), and the shape of a base curve (BC), are strictly defined. According to the contact lens package of the embodiments, the sticking (adhesion) of the silicone hydrogel contact lens to the packaging container is further effectively inhibited. Thus, the lens can be maintained at a satisfactory level over a prolonged period of time, and the breakage of the lens in use by a user can be inhibited.

The present invention is not limited to the foregoing embodiments. It will be obvious that various modifications may be made within the technical scope of the present invention.

EXAMPLES

Examples in which contact lens packages of the present invention are specifically produced and used will be described below as Examples.

[Contact Lens]

As commercial item 1, 1-DAY ACUVUE TruEye available from Johnson & Johnson was used. As pretreatment, 15 ml of a packaging solution and five lenses of the commercial item 1 were placed in a screw vial SV-20, available from Nichiden Rika Glass Co., Ltd. Liquid displacement was performed for 3 hours or more. Contact lenses composed of materials 1 to 4 were produced as follows: Polymerizable compositions formulated as listed in Table 1 were each placed in a contact lens mold that was composed of polypropylene and that had a contact lens shape. Materials 1 and 2 were each irradiated with light using a blue-fluorescent lamp for 15 minutes and then a high-luminance blue LED lamp for 15 minutes to produce a contact lens. Materials 3 and 4 were each irradiated with ultraviolet light using a high-pressure mercury lamp for 20 minutes to produce a contact lens. A urethane bond-containing polydimethylsiloxane macromonomer described in Table 1 has a structure represented by chemical formula (2). The contact lenses composed of materials 1, 2, and 4 were subjected to surface modification treatment with a plasma generator. The surface modification treatment was performed using $CO_2$ serving as a carrier gas in a reduced pressure state at an output of 80 W. The contact lens composed of material 3 was not subjected to surface modification treatment. In addition, a contact lens that had been subjected to atmospheric-pressure plasma treatment was produced. The polymerizable composition of material 1 formulated as listed in Table 1 was placed in the contact lens mold that was composed of polypropylene and that had a contact lens shape. The polymerizable composition was irradiated with light using a blue LED lamp for 12 minutes and then a high-luminance blue LED lamp for 15 minutes to produce a contact lens. The resulting contact lens was subjected to surface modification treatment with an atmospheric-pressure plasma treatment apparatus at atmospheric pressure (material 5).

In the case of materials 1 to 3, each of the lenses was immersed in the packaging solution for lenses in an amount of 2.8 ml per lens and allowed to stand for 3 hours to hydrate the lens. In the case of material 4, after the lens was immersed in deionized water in an amount of 2.2 ml per lens for 10 minutes, the lens was immersed in deionized water in an amount of 2.2 ml per lens for another 10 minutes and then immersed in a solution of Comparative example 1 in a 24-well plate in an amount of 2.2 ml per lens. Subsequently, the lens was sterilized with a high-pressure steam sterilizer SM-22, available from Yamato Scientific Co., Ltd., at 121° C. for 20 minutes. The lens composed of material 5 was hydrated by swelling the lens to equilibrium with the packaging solution described in Table 2 and deionized water. Then the lens was immersed in the solution of Example 2 in a blister for a contact lens and sterilized with a high-pressure steam sterilizer at 121° C. for 20 minutes, thereby providing a contact lens composed of material 5.

TABLE 1

| Components | Material 1 % by mass | Material 2 % by mass | Material 3 % by mass | Material 4 % by mass |
|---|---|---|---|---|
| Urethane bond-containing polydimethylsiloxane macromonomer | 5 | 15 | 33 | 36 |
| Tris (trimethylsilyloxy) silylpropyl methacrylate (TRIS) | 30 | 37 | 22 | 19 |
| N-vinyl-2-pyrrolidone(N-VP) | 41 | 30 | — | — |
| 1-methyl-3-methylene-2-pyrrolidone(N-MMP) | — | — | 34 | 34 |
| 2-methoxyethyl acrylate(2-MTA) | 24 | 18 | — | — |
| N,N-dimethylacrylamide(DMAA) | — | — | 11 | 11 |
| Allyl methacrylate(AMA) | 0.3 | 0.3 | — | — |
| Ethylene glycol dimethacrylate(EDMA) | — | — | 0.4 | 0.4 |
| 2-(2'-hydroxy-5'-methacryloyloxyethylphenyl)-2H-benzotriazole(HMEPBT) | 1 | 1 | — | — |
| 2-hydroxy-2-methyl-1-phenylpropan-1-one(HMPPO) | — | — | 0.4 | 0.4 |
| 2,4,6-trimethylbenzoyldiphenylphosphine oxide(TPO) | 0.6 | 0.6 | — | — |
| Copper phthalocyanine-containing polymethacrylic acid ester (BKH-1416) | 0.02 | 0.02 | — | — |

[Packaging Solutions of Examples 1 to 7]

Packaging solutions of examples were prepared in mixing proportions listed in Table 2. Each of the packaging solutions contained, as common components, NaCl and propylene glycol (PG) serving as isotonizing agents, sodium hydrogen phosphate hydrate and sodium dihydrogen phosphate serving as buffers, and edetate trisodium serving as a chelating agent. In each of Examples 1 to 4, a polyoxyethylene hydrogenated castor oil (HCO-60: linear alkyl chain having 17 carbon atoms, average addition mole number of oxyethylene=60) was used as a nonionic surfactant. In Example 5, a polyoxyethylene hydrogenated castor oil (HCO-40: linear alkyl chain having 17 carbon atoms, average addition mole number of oxyethylene=40) was used as a nonionic surfactant. In each of Examples 6 and 7, a polyoxyethylene hydrogenated castor oil (HCO-100: linear alkyl chain having 17 carbon atoms, average addition mole number of oxyethylene=100) was used as a nonionic surfactant.

[Packaging Solutions of Comparative examples 1 to 7]

Packaging solutions of comparative examples were prepared in mixing proportions listed in Table 2. In Comparative example 1, no nonionic surfactant was used. In each of Comparative examples 2 and 3, polysorbate 80 (linear alkyl chain having 17 carbon atoms, average addition mole number of oxyethylene=20) was used as a nonionic surfactant. In Comparative example 4, Pluronic L44 (linear alkyl chain: absent, average addition mole number of oxyethylene=20) was used as a nonionic surfactant. In Comparative example 5, Kolliphor P407 (linear alkyl chain: absent, average addition mole number of oxyethylene=196) was used as a nonionic surfactant. In Comparative example 6, Pluronic P123 (linear alkyl chain: absent, average addition mole number of oxyethylene=42) was used as a nonionic surfactant. In Comparative example 7, hydroxypropylmethyl cellulose (HPMC) TC-5 (linear alkyl chain: absent, average addition mole number of oxyethylene=0) was used as a nonionic surfactant.

(Evaluation of Sticking)

Each of the packaging solutions of Examples 1 to 7 and Comparative examples 1 to 7 was dispensed to a 24-well plate, available from Evergreen Scientific, composed of polypropylene in a volume of 2.2 ml per well. Each of the lenses composed of materials 1 to 5 was immersed therein. The 24-well plate in which the lenses were immersed was sterilized with a high-pressure steam sterilizer SM-22, available from Yamato Scientific Co., Ltd., at 121° C. for 20 minutes. After the sterilization, the sticking of the lenses to the container was evaluated based on whether the lenses were moved or not while the well plate was inclined at an angle of 30°. The packaging solutions in which the percentage of the lenses stuck was 20% or less were evaluated as "pass".

(Evaluation of Tensile Modulus of Elasticity)

Each lens material that had been subjected to sterilization treatment in the same way as the evaluation of sticking was processed with a punching blade into a dumbbell-shaped specimen (parallel section: 6 mm in length, 2 mm in width). The specimen immersed in an ISO physiological saline solution was placed in a constant-temperature water bath set at 20° C. (actually measured temperature: 20.0° C.) for conditioning. The thickness of the conditioned specimen was measured with a Litematic available from Mitutoyo Corporation. Both ends of the specimen were fixed to grippers of a Shimadzu Precision Universal Tester (Autograph AG-IS (MS), available from Shimadzu Corporation). The specimen was stretched at a crosshead speed of 100 mm/min until the specimen was broken. Stress at break was read. The tensile modulus of elasticity was calculated from the gradient of the tangent at the transformation starting point of a tensile stress-strain curve.

(Measurement of Relative Density (Lens))

The relative density of each of the lens materials was measured using a Sartorius density determination kit YDK 01 that had been subjected to sterilization treatment in the same way as the evaluation of sticking. An immersion liquid was placed in a beaker. The beaker was placed on a fixed support with the immersion liquid maintained at a predetermined temperature so as not to be in contact with a moving part of a balance. The mass W1 (g) of the lens in air at 20° C. was weighed to one decimal place in units of milligrams using an upper weighing dish of weighing dishes attached to the fixed support. Ten lenses for each material were used. Water on lens surfaces was wiped with absorbent paper before weighing. A thermometer was inserted into the immersion liquid. The temperature of the immersion liquid was confirmed to be 20° C. Each lens was placed on a lower weighing dish in such a manner that no air bubbles were attached to the lens. The mass W2 (g) in the immersion liquid was weighed to one decimal place in units of milligrams. The relative density was calculated from formula (1) using the density P (g/cm$^3$) of the immersion liquid at a predetermined temperature and the density K (g/cm$^3$) of water at a predetermined temperature:

$$\text{Relative density } S=P/K\times(W1/(W1-W2)) \quad \text{formula (1)}$$

(Measurement of Relative Density (Packaging Solution))

The mass M (g) of a Sprengel Ostwald pycnometer was measured to four decimal places with an electronic balance. One fine tube of the Sprengel Ostwald pycnometer was immersed in the packaging solution with a temperature that had been controlled in a constant-temperature water bath set at 20° C. for about 15 minutes. The liquid was sucked up to above a marked line. The temperature of the constant-temperature water bath set at 20° C. was confirmed to be the set temperature. The Sprengel Ostwald pycnometer was immersed therein for about 15 minutes. A piece of filter paper was attached to an end to adjust the front of the liquid to the marked line. The pycnometer was taken out from the constant-temperature water bath. The outside of the pycnometer was wiped well. Then the mass M1 (g) of the pycnometer was weighed with the electronic balance. By use of the same Sprengel Ostwald pycnometer, the same operation was performed with purified water to measure the mass M2 (g). The relative density d was calculated to three decimal places from formula (2). The density X at 20° C. was calculated to three decimal places from formula (3).

$$\text{Relative density } d=(M1-M)/(M2-M) \quad \text{formula (2)}$$

$$\text{Density } X=0.99704\times d \quad \text{formula (3)}$$

(Results and Discussion)

Table 2 summarizes the compositions of the packaging solutions and the percentage of the lenses stuck in examples and comparative examples. Table 3 summarizes the results of the relative densities of the lenses and the packaging solutions and the tensile moduli of elasticity (Young's moduli) of the lenses. As described in Tables 2 and 3, in the lenses composed of material 4, the sticking of the contact lenses to the packaging container did not occur, regardless of the packaging solutions. The reason for this is presumably that the lenses composed of material 4 have high Young's modulus and thus the contact area of each contact lens is not increased. In the lenses having Young's modulus of less than 1.4 MPa, the sticking occurred. In Comparative examples 1 to 7, it was found that the effect of inhibiting adhesion was not sufficiently provided. In contrast, in Examples 1 to 7, in which the nonionic surfactants (polyoxyethylene hydrogenated castor oils) were used, each of the nonionic surfactants containing the linear alkyl moiety having 12 or more carbon atoms and the oxyethylene moiety, the average addition mole number of oxyethylene being 30 or more, the results indicated that the effect of inhibiting the adhesion between the contact lenses and the packaging container was significantly high. It was found that the amount of the nonionic surfactant incorporated was preferably 0.001% or more by mass and 0.1% or less by mass. It was also found that when the average addition mole number of oxyethylene in the nonionic surfactant was in the range of 40 to 100, the effect of inhibiting the adhesion was provided. The results of Example 7 indicated that the incorporation of the nonionic surfactant used in the examples provided the effect of markedly inhibiting the adhesion even if another surfactant was incorporated. The difference in relative density between the silicone hydrogel contact lens and the packaging solution is preferably 0.1 or less. The results of the studies on the conditions of the surface modification treatment indicated that in the cases of the packaging solutions of the examples, the sticking of the contact lenses to the packaging container did not occur, whether the surface treatment was performed at atmospheric or reduced pressure. That is, it was found that the packaging solutions of the examples further inhibited the sticking, irrespective of the conditions of the surface treatment.

TABLE 2

| Evaluation of Sticking Test | | Example 1 % by mass | Example 2 % by mass | Example 3 % by mass | Example 4 % by mass | Example 5 % by mass | Example 6 % by mass | Example 7 % by mass | comparative example 1 % by mass |
|---|---|---|---|---|---|---|---|---|---|
| Common components | NaCl | 0.8 | ← | ← | ← | ← | ← | ← | ← |
| | Sodium hydrogen phosphate hydrate | 0.6 | ← | ← | ← | ← | ← | ← | ← |
| | Sodium dihydrogen phosphate | 0.04 | ← | ← | ← | ← | ← | ← | ← |
| | Edetate trisodium | 0.03 | ← | ← | ← | ← | ← | ← | ← |
| | PG | 0.1 | ← | ← | ← | ← | ← | ← | ← |
| Components of example | HCO-40 | — | — | — | — | 0.005 | — | — | — |
| | HCO-60 | 0.001 | 0.005 | 0.01 | 0.05 | — | — | — | — |
| | HCO-100 | — | — | — | — | — | 0.005 | 0.02 | — |
| Components of comparative example | Polysorbate 80 | — | — | — | — | — | — | — | — |
| | HPMC TC-5 | — | — | — | — | — | — | — | — |
| | Pluronic L44 | — | — | — | — | — | — | 0.005 | — |
| | Kolliphor P 407 | — | — | — | — | — | — | — | — |
| | Pluronic P123 | — | — | — | — | — | — | — | — |

TABLE 2-continued

| | | | | | | | | | |
|---|---|---|---|---|---|---|---|---|---|
| Percentage of the lenses stuck (%) | Commercial item 1 | 0% | 0% | 0% | 0% | 20% | 0% | 0% | 100% |
| | Material 1 | 0% | 0% | 0% | 0% | 0% | 0% | 0% | 100% |
| | Material 2 | 0% | 0% | 0% | 0% | 0% | 0% | 0% | 100% |
| | Material 3 | 20% | 20% | 0% | 20% | 20% | 0% | 20% | 100% |
| | Material 4 | 0% | 0% | 0% | 0% | 0% | 0% | 0% | 0% |
| | Material 5 (atmospheric-pressure plasma treatment) | — | 0% | — | — | — | — | — | 100% |

| Evaluation of Sticking Test | | comparative example 2 % by mass | comparative example 3 % by mass | comparative example 4 % by mass | comparative example 5 % by mass | comparative example 6 % by mass | comparative example 7 % by mass |
|---|---|---|---|---|---|---|---|
| Common components | NaCl | ← | ← | ← | ← | ← | ← |
| | Sodium hydrogen phosphate hydrate | ← | ← | ← | ← | ← | ← |
| | Sodium dihydrogen phosphate | ← | ← | ← | ← | ← | ← |
| | Edetate trisodium | ← | ← | ← | ← | ← | ← |
| | PG | ← | ← | ← | ← | ← | ← |
| Components of example | HCO-40 | — | — | — | — | — | — |
| | HCO-60 | — | — | — | — | — | — |
| | HCO-100 | — | — | — | — | — | — |
| Components of comparative example | Polysorbate 80 | 0.001 | 0.005 | — | — | — | — |
| | HPMC TC-5 | — | — | — | — | — | 0.005 |
| | Pluronic L44 | — | — | 0.005 | — | — | — |
| | Kolliphor P 407 | — | — | — | 0.001 | — | — |
| | Pluronic P123 | — | — | — | — | 0.001 | — |
| Percentage of the lenses stuck (%) | Commercial item 1 | 100% | 80% | 100% | 80% | 60% | 100% |
| | Material 1 | 60% | 20% | 80% | 100% | 20% | 20% |
| | Material 2 | 0% | 0% | 0% | 0% | 100% | 0% |
| | Material 3 | 40% | 100% | 100% | 80% | 20% | 0% |
| | Material 4 | 0% | 0% | 0% | 0% | 0% | 0% |
| | Material 5 (atmospheric-pressure plasma treatment) | — | — | — | — | — | — |

※ "←" means same value as left cell. "—" means not contained, or not examined.

TABLE 3

| Result of measurement of relative density (Lens) | Relative Density (20° C.) |
|---|---|
| Commercial item 1 | 1.043 |
| Material 1 | 1.060 |
| Material 2 | 1.052 |
| **Result of measurement of relative density (Packaging solution)** | **Relative Density (20° C.)** |
| Example 2 | 1.007 |
| Example 3 | 1.009 |
| Example 5 | 1.012 |
| Example 6 | 1.014 |
| **Evaluation of tensile modulus of elasticity** | **Tensile modulus of elasticity (MPa)** |
| Commercial item 1 | 0.6 |
| Material 1 | 0.4 |
| Material 2 | 0.9 |
| Material 3 | 1.2 |
| Material 4 | 1.4 |

INDUSTRIAL APPLICABILITY

The present invention can be used in the technical field of the production and distribution of contact lens packages.

The invention claimed is:

1. A contact lens package comprising:

a silicone hydrogel contact lens having a Young's modulus of 1.2 MPa or less;

a packaging container composed of a polypropylene; and a packaging solution containing a nonionic surfactant, the nonionic surfactant comprising a polyoxyethylene hydrogenated castor oil serving as the nonionic surfactant, the polyoxyethylene hydrogenated castor oil including a linear alkyl moiety having 12 or more carbon atoms and an oxyethylene moiety, the polyoxyethylene hydrogenated castor oil having an average addition mole number of oxyethylene of 30 or more per mole of the polyoxyethylene hydrogenated castor oil, and a concentration of the polyoxyethylene hydrogenated castor oil in the packaging solution is 0.001% or more by mass and 0.1% or less by mass.

2. The contact lens package according to claim 1, wherein a difference in relative density between the packaging solution and the silicone hydrogel contact lens is 0.1 or less.

3. The contact lens package according to claim 1, wherein the average addition mole number of oxyethylene is 30 or more and 100 or less.

4. The contact lens package according to claim 1, wherein the average addition mole number of oxyethylene is 40 or more and 100 or less.

5. The contact lens package according to claim 1, wherein the silicone hydrogel contact lens is made from a urethane bond-containing polydimethylsiloxane macromonomer.

6. The contact lens package according to claim 1, wherein the silicone hydrogel contact lens has a Young's modulus that is in a range of from 0.4 MPa to 1.2 MPa.

7. The contact lens package according to claim 1, wherein the concentration of the polyoxyethylene hydrogenated castor oil is 0.001% or more by mass and 0.08% or less by mass.

8. The contact lens package according to claim 1, wherein the concentration of the polyoxyethylene hydrogenated castor oil is 0.001% or more by mass and 0.02% or less by mass.

9. A method for producing a contact lens package, comprising:

sealing a silicone hydrogel contact lens and a packaging solution in a packaging container composed of a polypropylene, wherein the silicone hydrogel contact lens has a Young's modulus of 1.2 MPa or less, the packaging solution contains a nonionic surfactant, the nonionic surfactant comprising a polyoxyethylene hydrogenated castor oil serving as the nonionic surfactant, the polyoxyethylene hydrogenated castor oil including a linear alkyl moiety having 12 or more carbon atoms and an oxyethylene moiety, the polyoxyethylene hydrogenated castor oil having an average addition mole number of oxyethylene of 30 or more per mole of the polyoxyethylene hydrogenated castor oil, and a concentration of the polyoxyethylene hydrogenated castor oil in the packaging solution is 0.001% or more by mass and 0.1% or less by mass.

* * * * *